United States Patent
Duan et al.

(10) Patent No.: US 7,839,499 B2
(45) Date of Patent: Nov. 23, 2010

(54) HYDROGEN SENSOR

(75) Inventors: Yixiang Duan, Los Alamos, NM (US); Quanxi Jia, Los Alamos, NM (US); Wenqing Cao, Katy, TX (US)

(73) Assignee: Los Alamos National Security, LLC, Los Alamos, NM (US)

( * ) Notice: Subject to any disclaimer, the term of this patent is extended or adjusted under 35 U.S.C. 154(b) by 181 days.

(21) Appl. No.: 12/069,971

(22) Filed: Feb. 13, 2008

(65) Prior Publication Data

US 2009/0201500 A1 Aug. 13, 2009

(51) Int. Cl.
*G01J 3/30* (2006.01)
(52) U.S. Cl. ..................................... 356/316
(58) Field of Classification Search ............ 356/316; 73/31.05
See application file for complete search history.

(56) References Cited

U.S. PATENT DOCUMENTS

| 5,414,324 A | 5/1995 | Roth et al. |
| 6,620,247 B2 * | 9/2003 | Ebe et al. ............ 118/689 |
| 2002/0098713 A1 * | 7/2002 | Henley et al. ............ 438/776 |

OTHER PUBLICATIONS

Park et al., "An Atmospheric Pressure Plasma Source," Applied Physics Letters, vol. 76, No. 3, Jan. 2000, pp. 288-290.
Stark et al., "Direct Current High-Pressure Glow Discharges," Journal of Applied Physics, vol. 85, No. 4, Feb. 1999, pp. 2075-2080.
Jin et al., "A Low-Power, Atmospheric Pressure, Pulsed Plasma Source for Molecular Emission Spectrometry," Anal. Chem., vol. 73, No. 2, Jan. 2001, pp. 360-365.
Duan et al., "Capillary-Discharge-Based Portable Detector for Chemical Vapor Monitoring," Review of Scientific Instruments, vol. 74, No. 5, May 2003, pp. 2811-2816.
Jin et al., "Simple, Sensitive Nitrogen Analyzer Based on Pulsed Miniplasma Source Emission Spectrometry," Review of Scientific Instruments Dec. 2003, vol. 74, No. 12, pp. 5156-5160.

* cited by examiner

*Primary Examiner*—Tarifur Chowdhury
*Assistant Examiner*—Abdullahi Nur
(74) *Attorney, Agent, or Firm*—Samuel L. Borkowsky

(57) ABSTRACT

A hydrogen sensor for detecting/quantitating hydrogen and hydrogen isotopes includes a sampling line and a microplasma generator that excites hydrogen from a gas sample and produces light emission from excited hydrogen. A power supply provides power to the microplasma generator, and a spectrometer generates an emission spectrum from the light emission. A programmable computer is adapted for determining whether or not the gas sample includes hydrogen, and for quantitating the amount of hydrogen and/or hydrogen isotopes are present in the gas sample.

10 Claims, 10 Drawing Sheets

HYDROGEN SENSOR

STATEMENT REGARDING FEDERAL RIGHTS

This invention was made with government support under Contract No. DE-AC52-06NA25396 awarded by the U.S. Department of Energy. The government has certain rights in the invention.

FIELD OF THE INVENTION

The present invention relates generally to a hydrogen sensor for detecting hydrogen and/or isotopes deuterium and tritium.

BACKGROUND OF THE INVENTION

Hydrogen is a colorless, odorless gas used in petroleum reforming, semiconductor manufacturing, cryogenic cooling, chemical synthesis, fuel cells, rocket engines, hydrogen storage, fuel cells, automobiles, fire warning systems, leakage detection, nuclear reactors, sensing environmental contamination, and in biomedical procedures. Hydrogen has also been recognized as an alternative, clean, and renewable energy source. Hydrogen can penetrate into metals and affect their strength and durability. There are also risks of explosion in systems employing hydrogen. For these and other reasons, hydrogen sensors such as electrochemical sensors, metal-oxide resistive sensors, optical fiber sensors, and mass spectrometric sensors have been developed over the years that can monitor the concentration of hydrogen.

Electrochemical hydrogen sensors use a liquid electrolyte and a gas permeable membrane for hydrogen to reach the electrolyte. These sensors can operate from 0.02% to 100% by volume. Exposure of the membrane to cryogenic or time-varying temperatures can affect gas diffusion and make the sensor unreliable.

Metal oxide-resistive sensors rely on a change in electrical conductivity due to an interaction between surface species such as oxide, protons, and hydroxide and hydrogen. In many cases, these types of sensors need to operate at elevated temperatures for effective detection of hydrogen.

Optical fiber sensors utilize the absorption change of an evanescent field in the clad region near the surface of the core of the fiber. In most of these sensors, a thin palladium or palladium alloy layer is usually employed as the transducer, because palladium allows the selective detection of hydrogen. The refractive index of a thin palladium layer changes when it is exposed to hydrogen. By monitoring the optical power transmission of a Pd/Pt-coated optical fiber, one can detect the refractive index changes in the Pd layer, and from this, the hydrogen concentration. This type of sensor has limited sensitivity and reliability.

Mass spectrometers are sensitive and have good linearity over a wide dynamic range. However, the complexity and high cost of mass spectrometers requires skilled operators and special sampling systems for effective hydrogen monitoring. Memory effect can also be a problem in mass spectrometric technology because a vacuum system is used for detection.

SUMMARY OF THE INVENTION

In accordance with the purposes of the present invention, as embodied and broadly described herein, an aspect of the present invention relates to a hydrogen sensor including: a sampling line for receiving a gas sample and sending the gas sample to a microplasma generator; a microplasma generator for receiving the gas sample from the sampling line and providing energy to the gas sample sufficient to produce light emission from hydrogen in the gas sample; a power supply for supplying power to the microplasma generator; a spectrometer in communication with the microplasma generator for obtaining a light emission spectrum from the gas sample; and a programmable computer in communication with said spectrometer and adapted for analyzing the light emission spectrum to determine whether or not hydrogen is present in the gas sample.

BRIEF DESCRIPTION OF THE DRAWINGS

The accompanying drawings, which are incorporated in and form a part of the specification, illustrate the embodiments of the present invention and, together with the description, serve to explain the principles of the invention. In the drawings.

DETAILED DESCRIPTION

The invention is concerned with hydrogen detection and quantitation. Hydrogen detection means detection of hydrogen atoms and/or its isotopes (deuterium, tritium) in a gas sample. Hydrogen quantitation means: (i) determining how much hydrogen is in the gas sample, or (ii) determining how much of at least one hydrogen isotope is in the gas sample, or (iii) determining how much hydrogen and at least one of its isotopes is in the gas sample.

Figure 1:
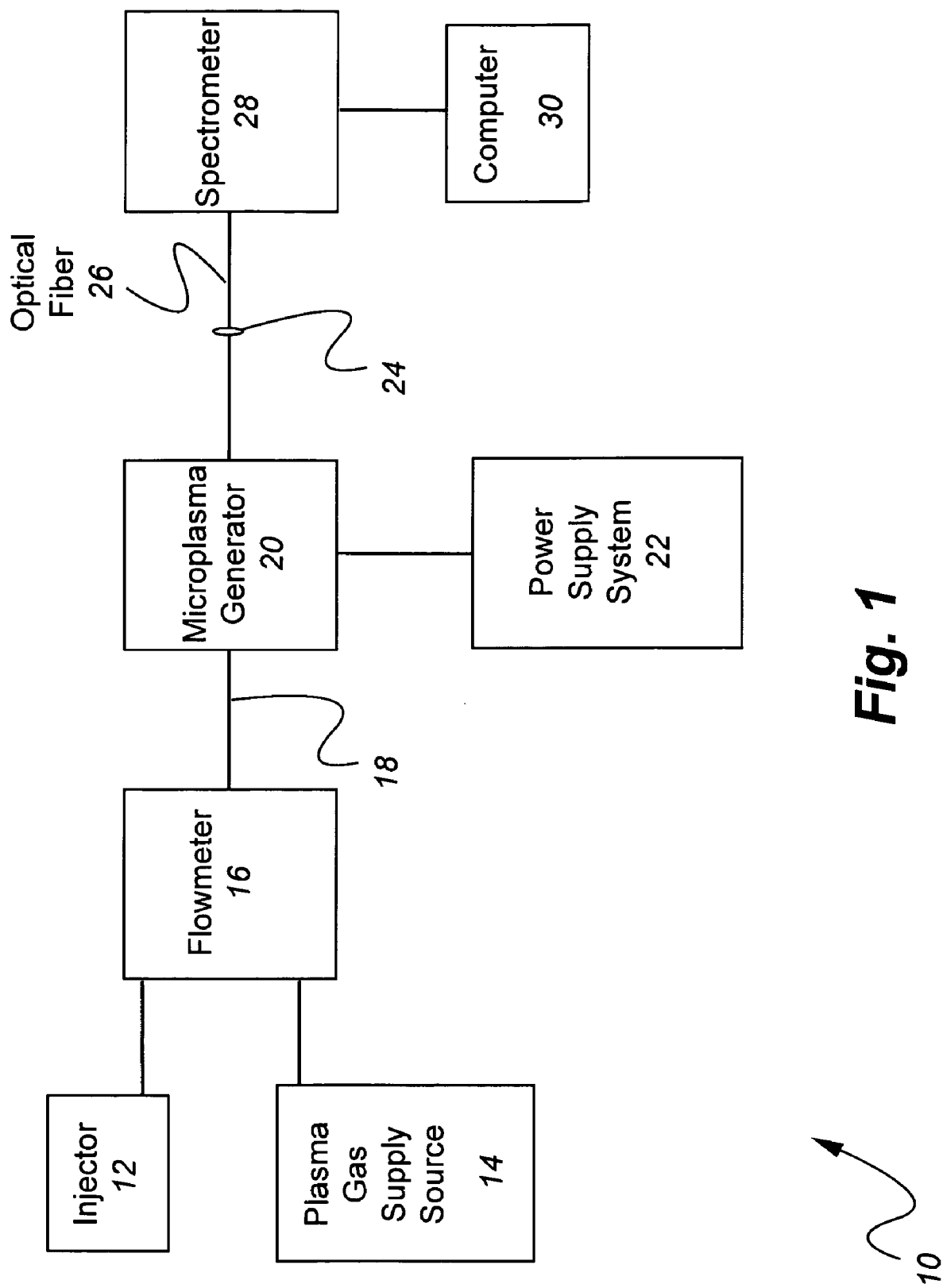
FIG. 1 shows a schematic representation of an embodiment hydrogen sensor of the invention.

Reference will now be made in detail to embodiments of the invention. Similar or identical structure is identified using identical callouts. A schematic diagram of an embodiment hydrogen sensor of the invention is shown in FIG. 1. The hydrogen sensor 10 includes an injector through which a gas sample is injected by syringe into the hydrogen sensor. A microplasma generator generates a microplasma (i.e. a plasma having a discharge volume on the microliter scale) from plasma gas; the plasma gas excites the gas sample and generates light emission from hydrogen in the gas sample. A power supply system, preferably a small one, supplies energy needed for generating and sustaining the microplasma. A spectrometer, preferably a small one, produces emission spectra from the light emission from hydrogen. During operation, a gas sample is injected through injector 12 into hydrogen sensor 10. The flow of the gas sample and plasma gas is regulated using a flowmeter/controller system 16 and moves through the sampling line 18 to microplasma generator 20 where plasma forms. Power supply system 22 provides the necessary power to the microplasma generator 20. The optical emission generated from excited hydrogen produced in microplasma generator 20 is collected using collimating lens 24, and is transmitted through optical fiber 26 to spectrometer 28. In a preferred embodiment, a palm-sized, high-resolution spectrometer coupled to a small, linear, charge coupled detector (CCD) array is used. Computer software with advanced acquisition and display function was used for data collection and storage. Computer 30 is adapted to process the spectral data obtained from spectrometer 18 to determine any of the following: (i) how much normal hydrogen is in the gas sample, (ii) how much of at least one hydrogen isotope is in the gas sample, and (iii) how much normal hydrogen and at least one of its isotopes is in the gas sample.

Figure 2A:
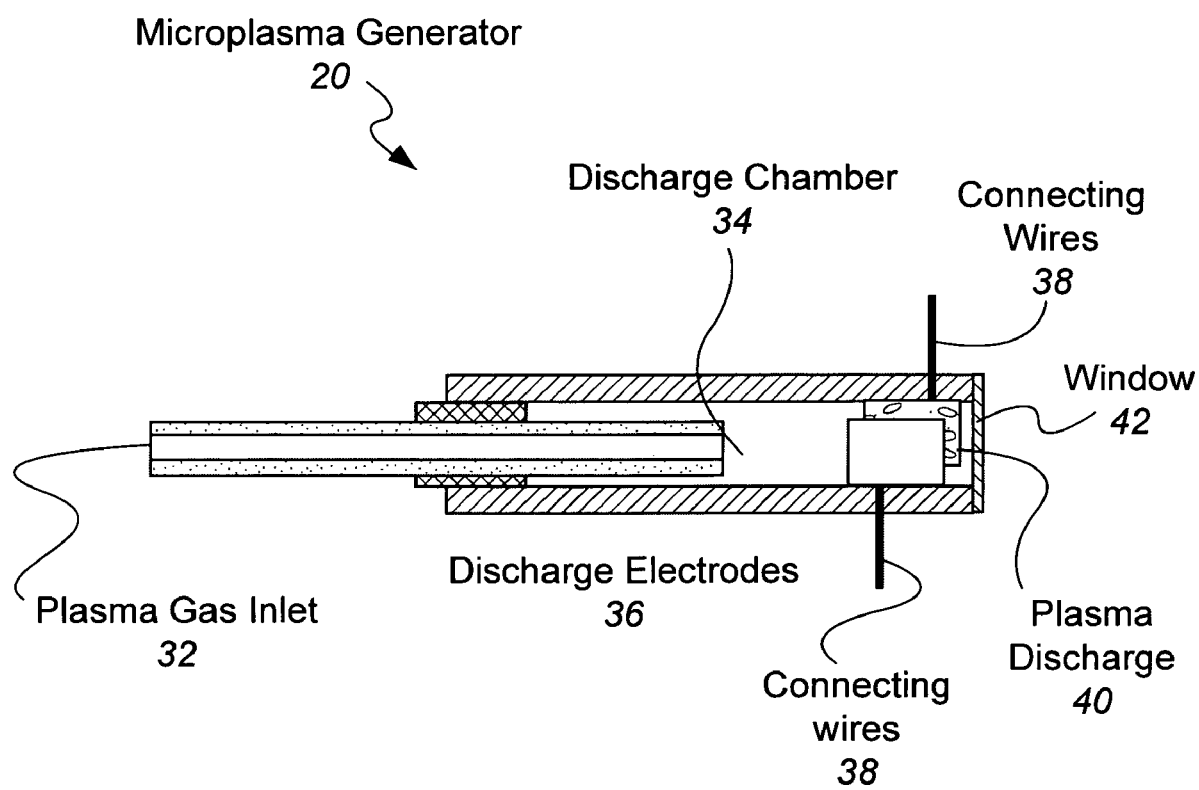
FIG. 2a-b shows sketches of an embodiment microplasma generator of the hydrogen sensor of FIG. 1.
Figure 2B:
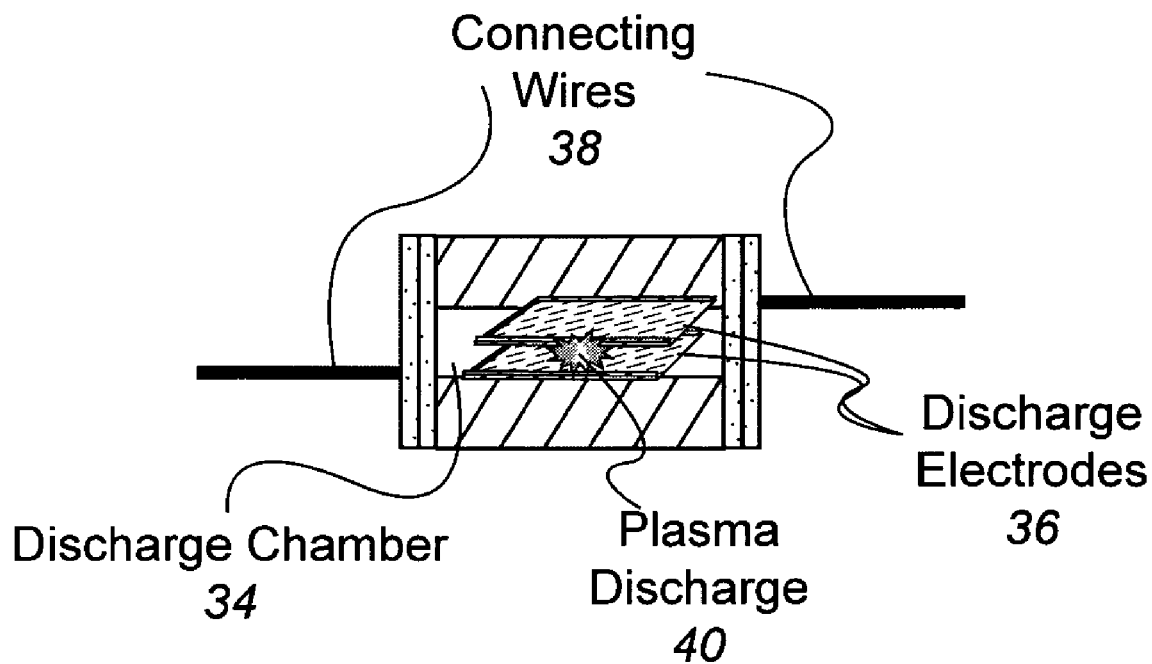

FIGS. 2a and 2b show a side view sketch and an end view sketch, respectively, of embodiment microplasma generator 20. FIGS. 2a-b show microplasma generator 20 includes inlet 32 for plasma gas and sample to enter. Microplasma generator 20 includes discharge chamber 34. Plasma gas entering discharge chamber 34 is subjected to a potential from discharge electrodes 36 sufficient for converting at least a portion of the plasma gas into plasma. Microplasma generator 20 also includes connecting wires 38, which connect electrodes 36 to power supply system 22. Plasma 40 generated in microplasma generator 20 interacts with the gas sample. If normal hydrogen and/or isotopes thereof are present in the gas sample, the plasma provides energy to the gas sample sufficient to electronically excite hydrogen in the gas sample. The electronically excited hydrogen emits light that exits the microplasma generator through optional discharge window 42, and is collected and transmitted to the spectrometer. A preferred microplasma generator of the invention employs ceramic materials because the plasma stability is improved when ceramic materials are used instead materials that are less tolerant to heat.

Preferably, discharge electrodes 36 are mechanically fixed on the discharge chamber wall. In a preferred embodiment, discharge electrodes 36 are two small flat electrodes oriented face to face. The total discharge produced using these electrodes is preferably at about the microliter level. The microplasma can be maintained at atmospheric pressure with just a small amount of plasma gas (argon or helium, for example). The microplasma is sustained in a very small volume for efficient collection of the optical emission beam.

In a preferred embodiment, microplasma generator 20 was designed and built within a narrow discharge chamber in which two metal plate electrodes were bonded to the chamber walls. The electrodes were placed face to face. Discharge chamber was measured at about 500 micrometers ("µm") in height×500 µm in width×600 µm in depth for a volume of about 150 nanoliters ("nL"). A DC voltage was applied to the electrodes for atmospheric pressure plasma generation. A collimate lens was used to collect the light emitted from the rectangular plasma chamber and focus the beam into an optical fiber. The optical emission was guided to an OCEAN OPTICS USB2000 spectrometer system (Ocean Optics, Dunedin, Fla.) including a linear CCD-array detector that was used for simultaneous detection of the whole spectrum from about 200 nanometers ("nm") to about 1100 nm. A notebook computer was connected to the spectrometer with a USB cable for display and data processing. All the experiments were performed at room temperature and atmospheric pressure. Unless otherwise noted, the following description relates to testing performing using this embodiment.

Figure 3:
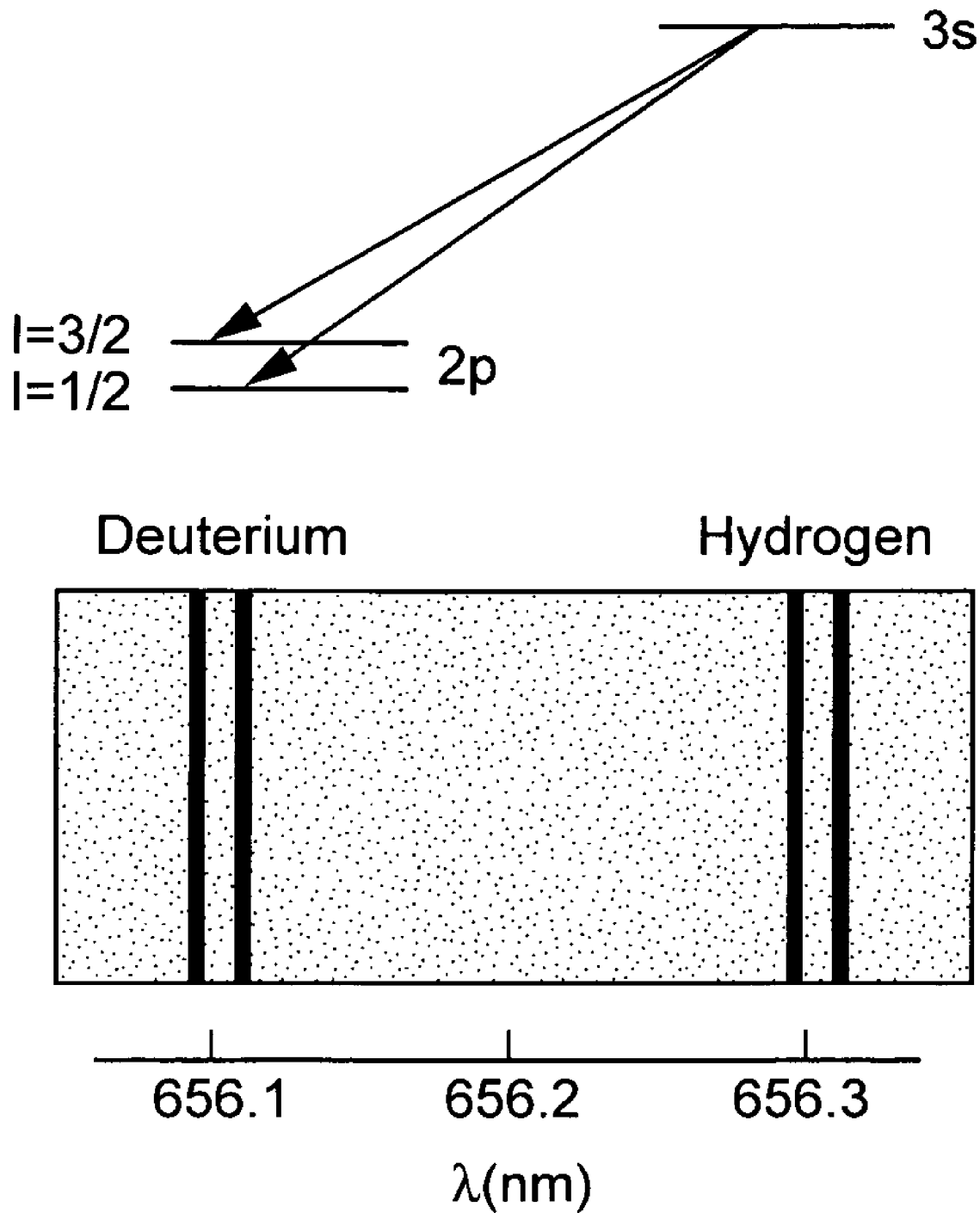
FIG. 3 shows an energy diagram for hydrogen and deuterium on the $\alpha$ line with an isotope shift of about 0.18 nanometers (nm).

Hydrogen and its isotopes produce the following three major emission lines: $\alpha$ (656.3 nm, red), $\beta$ (486.1 nm, blue), and $\gamma$ (434.1 nm, violet). These lines have been used in the past for quantitative detection of hydrogen. FIG. 3 schematically illustrates splitting of the $\alpha$ emission line, with an isotope shift (hydrogen, deuterium) of about 0.18 nm. In a preferred embodiment hydrogen sensor using a high-resolution spectrometer, these isotopes are easily resolvable.

Figure 4:
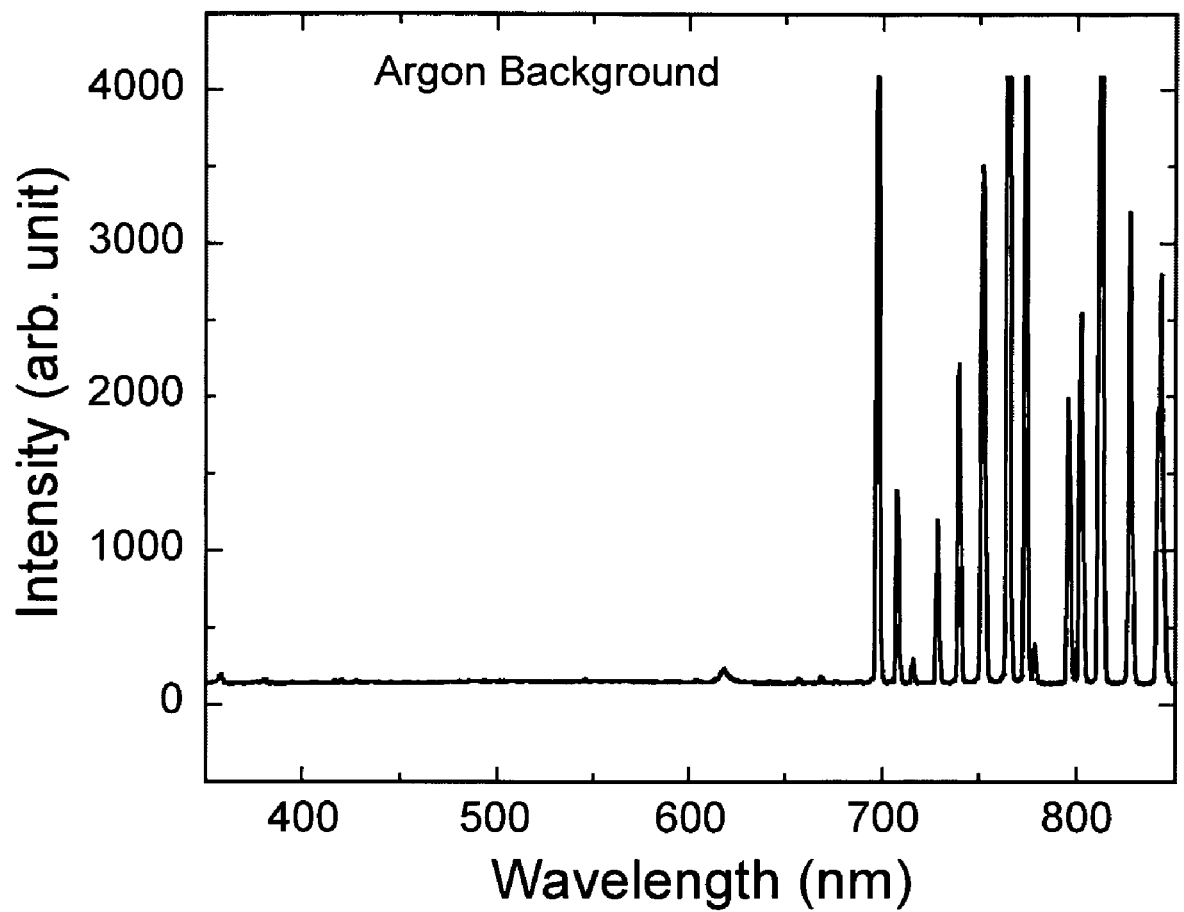
FIG. 4 shows an argon background spectrum for the microplasma device.
Figure 5:
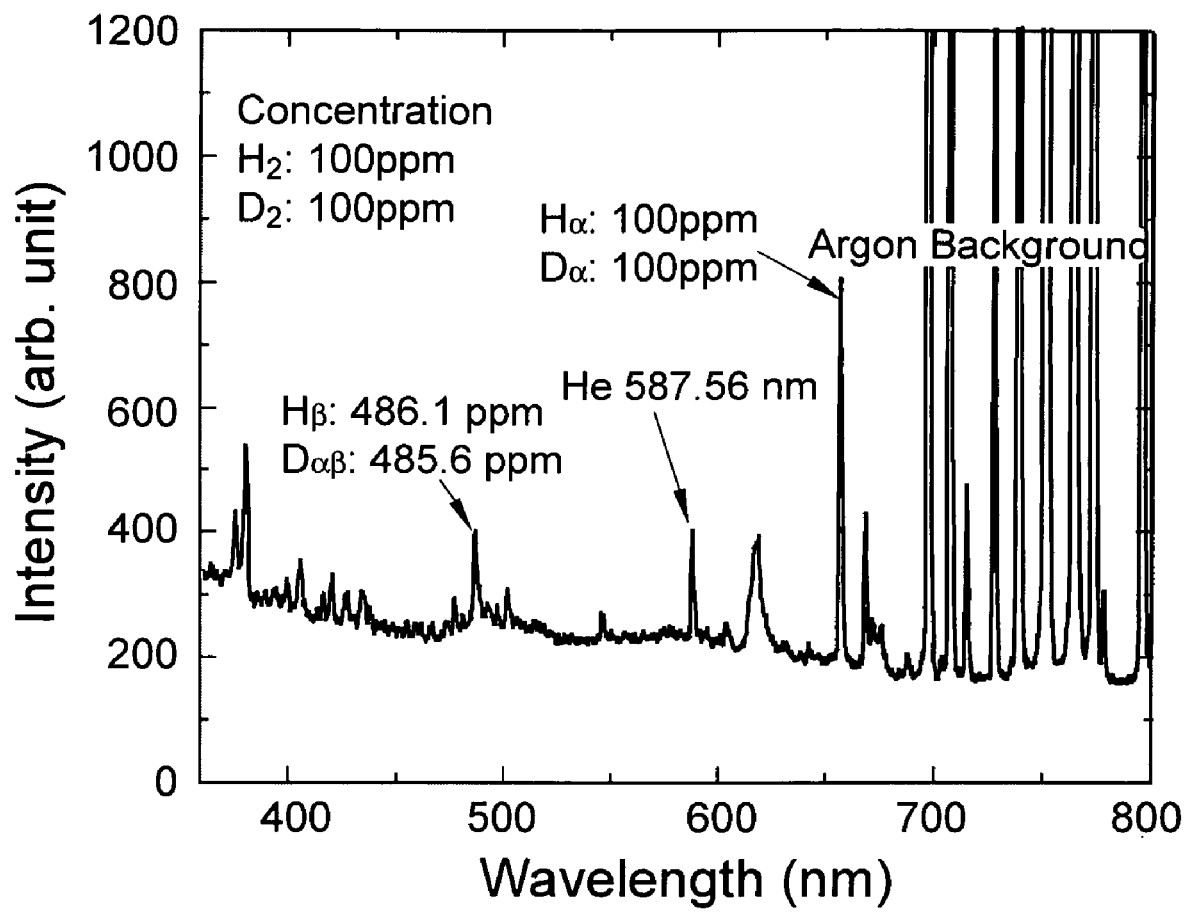
FIG. 5 shows a spectrum demonstrating detection of a trace amount (100 ppm) of hydrogen and deuterium in a gas sample.

In a typical set of test conditions, hydrogen sensor 10 operates at atmospheric pressure at a current of about 16 milliamperes ("mA") with an argon flow rate of 1000 cubic centimeters per minute ("cc/min"). A background emission of the argon plasma in the wavelength region between 300 and 900 nm is collected first (see FIG. 4). After obtaining the background emission, hydrogen is introduced, which results in generation and detection of the $\alpha$ and $\beta$ emission lines for hydrogen. FIG. 5 shows a typical hydrogen spectrum from 300 nm to 800 nm. Although the background peaks generated from argon plasma gas are significant, the clear spectral line profiles for $\alpha$ and $\beta$ emission lines demonstrate that the spectral influences from the background are minimal in detection hydrogen and its isotope deuterium.

Figure 6:
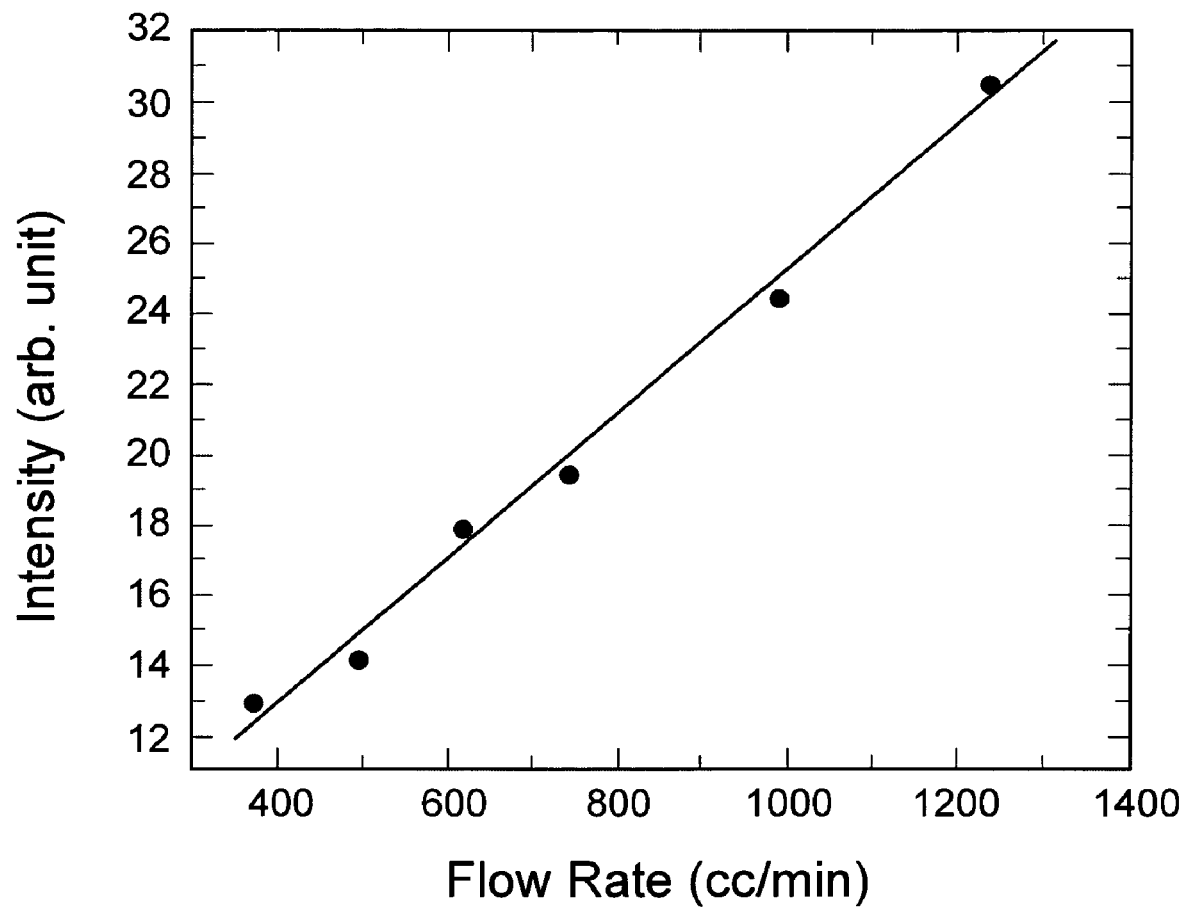
FIG. 6 shows a graph of intensity versus plasma gas flow rate. The graph demonstrates the influence of plasma gas flow rate.
Figure 7:
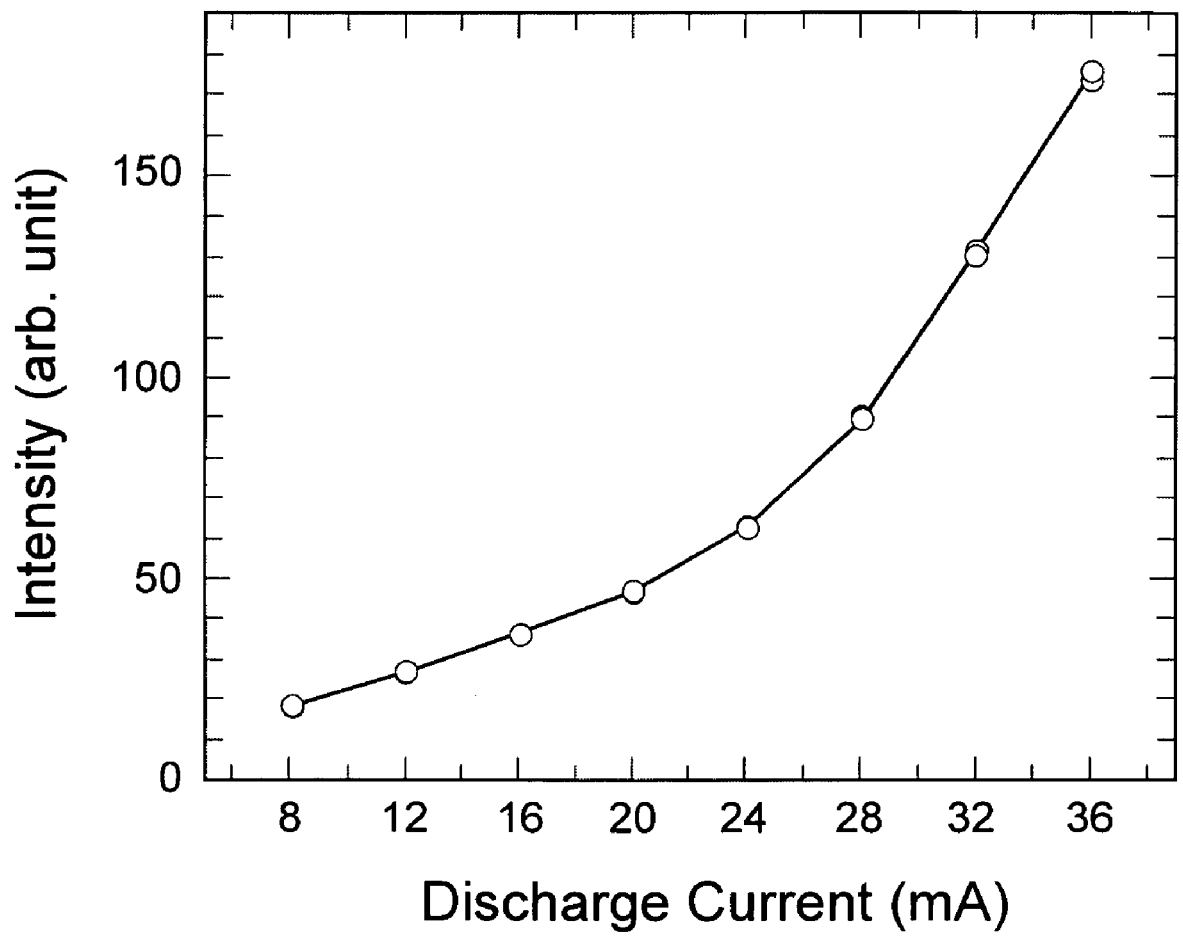
FIG. 7 shows a graph of intensity versus discharge current. The graph shows that the excitation becomes enhanced as the discharge current increases.

FIG. 6 graphically shows the influence of the plasma gas flow rate on signal intensity. An almost linear shape was obtained with plasma gas flow from 380 cubic centimeters per minute ("cc/min") to about 1250 ml/min. The relationship between the signal intensity and discharge current was also investigated by maintaining the argon plasma gas flow rate at about 1000 cc/min and the hydrogen/deuterium concentrations at 111 ppm, and then recording the influence of discharge current on signal intensity. The maximum discharge current was about 36 mA. FIG. 7 shows the relationship of plasma discharge current with the signal intensity. As FIG. 7 shows, the signal intensity is increased with the increase of the discharge current. Therefore, excitation of hydrogen is enhanced as the discharge current increases.

The stability of the plasma source for the preferred embodiment hydrogen sensor was also tested. The relative standard deviation ("RSD") was about 3.5% for the hydrogen $\alpha$ emission line. The detection limits were also estimated for the hydrogen $\alpha$ emission line. Based on the RSD and the signal intensity, a detection limit of about 5 ppm was estimated for the preferred embodiment hydrogen sensor. This limit could be improved using an even higher resolution spectrometer and better control of the microplasma generator. The hydrogen detection limit of about 5 ppm of the preferred embodiment hydrogen sensor is comparable to the reported detection limits using a mass spectrometer. The preferred embodiment sensor, however, is portable, can be used in the field, and much less expensive.

Figure 8:
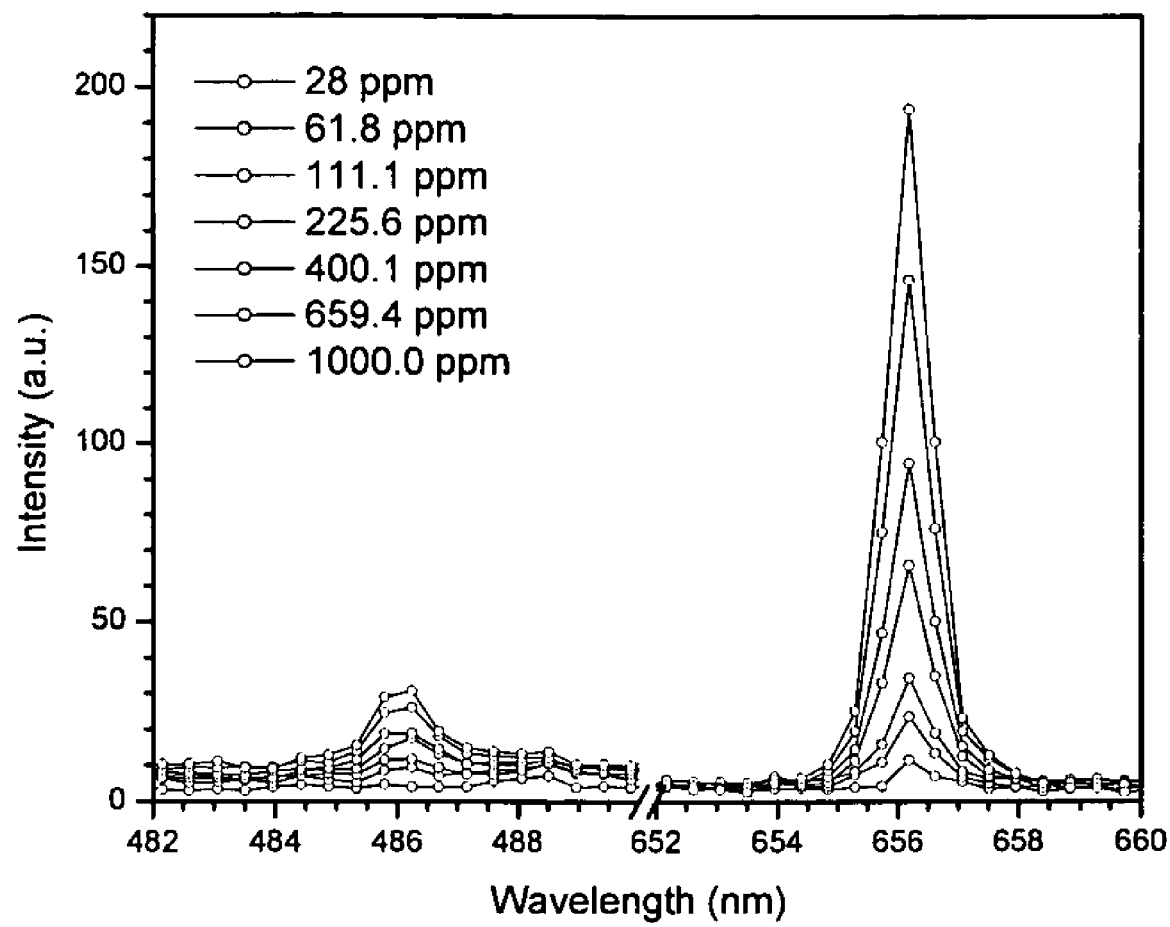
FIG. 8 shows a spectrum demonstrating hydrogen/deuterium signal response to the concentration changes from 28 ppm to 1000 ppm
Figure 9:
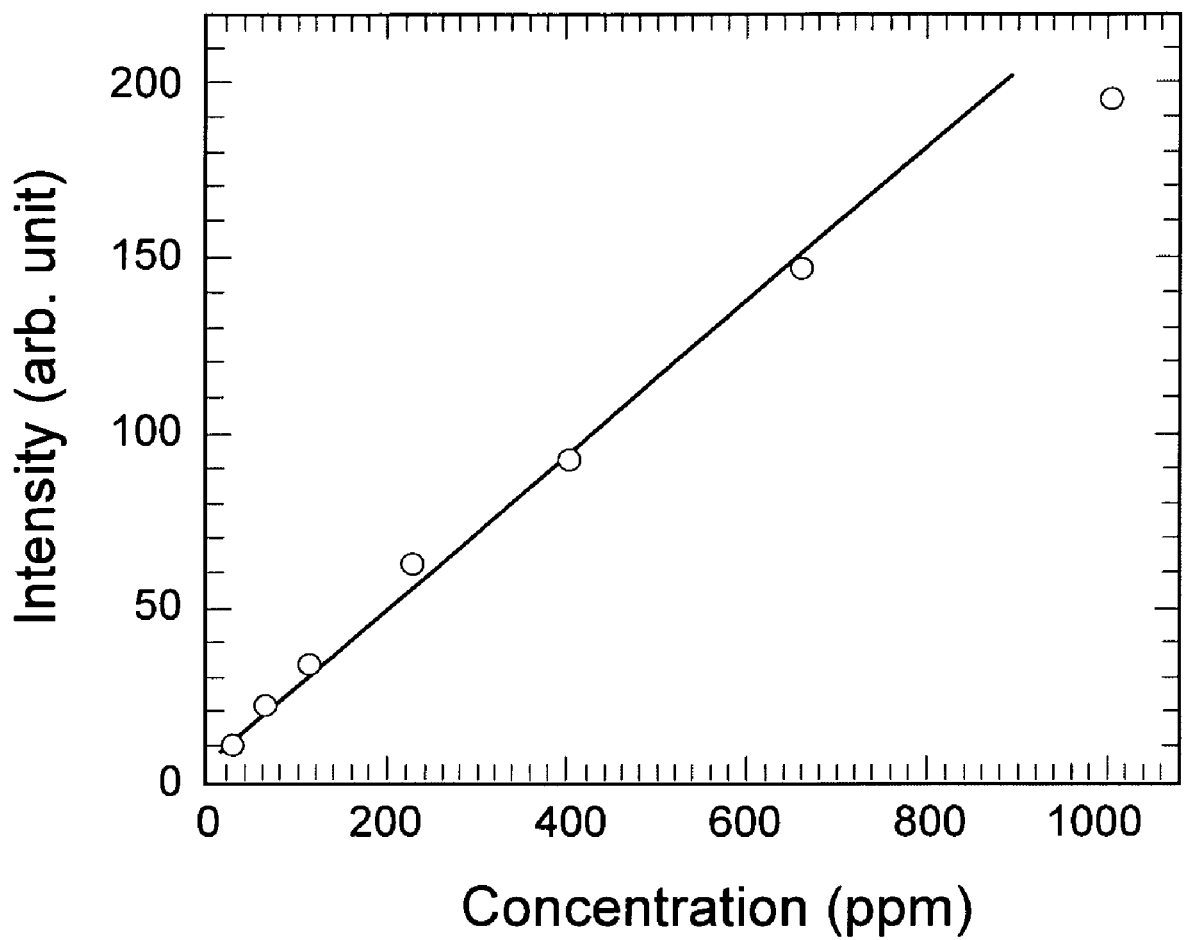
FIG. 9 shows a calibration curve for hydrogen detection in a concentration range from 18 parts per million ("ppm") to 800 ppm

In another embodiment, one employing a low-resolution spectrometer, the emission intensities of the hydrogen $\alpha$ and $\beta$ lines with different concentrations of hydrogen and deuterium were measured. FIG. 8 shows several spectra obtained for concentrations of hydrogen and deuterium varying from about 28 parts per million ("ppm") to about 1000 ppm. As the spectra show, the isotopic contributions from hydrogen and deuterium cannot be distinguished using this embodiment because the resolution of the spectrometer is too low. In order to resolve the emission lines for hydrogen and deuterium isotopes, a higher resolution spectrometer, one with resolution better than 0.1 nanometers, should be used for isotopic detection. However, this embodiment can still be used to determine the concentration of normal hydrogen in a gas sample. FIG. 9 shows a calibration curve for this embodiment sensor in a concentration range from 18 ppm to 1000 ppm for normal hydrogen.

In summary, a hydrogen sensor employing a microplasma that excites hydrogen and produces detectable light emission from the hydrogen in a gas sample allows for hydrogen detection and quantitation. The detection limit of 5 ppm is comparable to that reported using other more complex and expensive sensors. The sensor may be integrated into a handheld device for daily and routine monitoring of hydrogen.

The foregoing description of the invention has been presented for purposes of illustration and description and is not intended to be exhaustive or to limit the invention to the precise form disclosed, and obviously many modifications and variations are possible in light of the above teaching.

The embodiments were chosen and described in order to best explain the principles of the invention and its practical application to thereby enable others skilled in the art to best utilize the invention in various embodiments and with various modifications as are suited to the particular use contemplated. Although the invention has been disclosed with reference to its preferred embodiments, from reading this description those of skill in the art can appreciate changes and modifications that may be made which do not depart from the scope and spirit of the invention as described above and claimed hereafter. It is intended that the scope of the invention be defined by the claims appended hereto.

What is claimed is:

1. A hydrogen sensor, comprising:
a sampling line for receiving a gas sample;
a plasma gas source;
a plasma gas line for receiving plasma gas from the plasma gas source;
a microplasma generator that receives the gas sample and plasma gas and provides energy to the plasma gas sufficient to create an atmospheric pressure microplasma therefrom, the atmosphere microplasma having a discharge volume on the microliter scale and having energy sufficient to electronically excite hydrogen present in the gas sample, thereby producing light emission from hydrogen present in the gas sample;
a DC power supply for supplying power to the microplasma generator,
a spectrometer in communication with the microplasma generator for obtaining a light emission spectrum from hydrogen present in the gas sample, and in communication with said spectrometer,
a programmable computer adapted for analyzing the light emission spectrum to determine whether or not hydrogen is present in the gas sample.

2. The hydrogen sensor of claim 1, further comprising a fiber optic cable for communicating the light emission from the microplasma generator to the spectrometer.

3. The hydrogen sensor of claim 1, wherein said programmable computer also determines the amount of $H_2$ present in the gas sample.

4. The hydrogen sensor of claim 1, wherein said programmable computer determines the amount of at least one hydrogen isotope present in the gas sample.

5. The hydrogen sensor of claim 1, wherein said programmable computer determines the amount of $H_2$ and the amount of one other hydrogen isotope present in the sample.

6. The hydrogen sensor of claim 1, wherein said programmable computer determines the amount of $H_2$, $D_2$, and $T_2$ present in the sample.

7. The hydrogen sensor of claim 1, wherein said spectrometer comprises a low-resolution spectrometer or a high-resolution spectrometer.

8. The hydrogen sensor of claim 1, wherein the plasma gas comprises helium argon, nitrogen, or mixtures thereof.

9. The hydrogen sensor of claim 1, wherein said microplasma generator comprises a ceramic material.

10. The hydrogen sensor of claim 1, wherein said microplasma generator comprises a discharge chamber wall and two flat discharge electrodes attached to the discharge chamber wall.

* * * * *